United States Patent [19]
Gram et al.

[11] Patent Number: 5,425,276
[45] Date of Patent: Jun. 20, 1995

[54] MATERIAL TESTING SYSTEM PROVIDING SIMULTANEOUS FORCE LOADS

[75] Inventors: Martin M. Gram, St. Louis Park; Carl G. Larsen, Minneapolis; Han-sheng Chen, Eden Prairie; F. Joseph Albright, Minnetonka, all of Minn.

[73] Assignee: MTS Systems Corporation, Eden Prairie, Minn.

[21] Appl. No.: 142,518

[22] Filed: Oct. 26, 1993

[51] Int. Cl.[6] .................................. G01N 3/08
[52] U.S. Cl. ........................... 73/816; 73/856; 73/860; 73/781
[58] Field of Search ............... 73/816, 798, 855, 856, 73/857, 858, 859, 860, 826, 828, 837, 818, 808

[56] References Cited

U.S. PATENT DOCUMENTS

| | | | |
|---|---|---|---|
| 2,611,966 | 9/1952 | Rebman | 73/760 |
| 2,750,795 | 6/1956 | Federn | 73/816 |
| 2,763,149 | 9/1956 | Long et al. | 73/816 |
| 3,190,007 | 6/1965 | De Nicola et al. | 73/760 |
| 3,575,045 | 4/1971 | Knights | 73/860 |
| 3,590,631 | 7/1971 | Gonze | 73/794 |
| 4,478,086 | 10/1984 | Gram | 73/781 |
| 4,848,161 | 7/1989 | van der Kuur | 73/760 |
| 4,869,112 | 9/1989 | Gram et al. | 73/856 |
| 5,095,757 | 3/1992 | Larsen et al. | 73/857 |

FOREIGN PATENT DOCUMENTS 2081457  2/1982  United Kingdom .

OTHER PUBLICATIONS

"Dynamic Testing Method For Thin Plate With Sinusoidal Pneumatic Excitation", Yamamoto et al. Transactions of National Research Institute for Metals, vol. 16, No. 1, Jan. 1974, pp. 7–15.
Product Specification, Series 319 Axial/Torsional Load Units, MTS Corporation, 1991.

Primary Examiner—Richard E. Chilcot, Jr.
Assistant Examiner—James M. Olsen
Attorney, Agent, or Firm—Westman, Champlin & Kelly

[57] ABSTRACT

A material test system capable of applying multiple force load components simultaneously includes a first actuator connected in parallel with a spring element. The first actuator and the spring element in turn are connected in series with the test specimen and a second actuator. The spring element is substantially rigid in order to transfer the force load from the second actuator to the test specimen yet substantially compliant in order to allow transfer of the force load from the first actuator to the test specimen.

24 Claims, 7 Drawing Sheets

MATERIAL TESTING SYSTEM PROVIDING SIMULTANEOUS FORCE LOADS

BACKGROUND OF THE INVENTION

The present invention relates to a material testing system for applying force loads to a test specimen. More particularly, the present invention relates to material testing system that applies multiple force loads simultaneously.

The physical testing of materials by taking a test specimen and applying tension and/or compressive loads using an actuator is well known. Commonly, a single actuator is used, which if properly controlled can apply a single time varying load. However, the loading upon these materials when used in complex machinery is rarely from a single source. Typically, there exist multiple load sources each of which apply time varying loads of different frequencies.

Accordingly, testing machines have ben developed to apply multiple force loads simultaneously. United Kingdom Patent Application GB 2081457A discloses one such machine which includes a spring element interposed between two actuators, the first actuator being connected to the test specimen and the second actuator being connected to the test frame. As disclosed, the first actuator applies cyclical loads having a lower fundamental frequency and greater amplitude than the second actuator. However, this series connection orientation of the actuators and spring element requires that the second actuator must be capable of transferring the high amplitude loads of the first actuator.

SUMMARY OF THE INVENTION

A material test system capable of applying multiple force load components simultaneously includes a first actuator connected in parallel with a spring element. The first actuator and the spring element in turn are connected in series with the test specimen and a second actuator. The spring element is substantially rigid in order to transfer the force load from the second actuator to the test specimen yet substantially compliant in order to allow transfer of the force load from the first actuator to the test specimen.

In an embodiment of the test system, the test specimen is held at opposite ends by two grip assemblies. Preferably, the grip assemblies provide a preload force with each grip assembly having a gripping portion gripping the test specimen and an actuator portion operating the gripping portion. The actuator portion includes a piston that is displaceable relative to a chamber in a housing. A support column extends from the piston, the first actuator being mounted to the support column on end opposite the piston. The first actuator in turn is connected to the gripping portion.

Preferably, the spring element is connected between the gripping portion and the actuator portion and comprises two parallel springs. In a first embodiment, the springs include an inner spring tube surrounding the support column with a plurality of spring columns positioned at equal angular intervals about the spring column, while in a second embodiment, the spring columns are replaced with an outer spring tube surrounding the inner spring tube.

The material testing system applies simultaneous force loads, preferably sinusoidal wherein each force load has a different frequency with the first actuator applying a high frequency, low amplitude force load, and the second actuator applying a low frequency, high amplitude force load. By using a spring element that is capable of transferring the high amplitude force load of the second actuator, the first actuator need only be designed to transfer the low amplitude force load of the first actuator and the low deflection of the spring element.

DETAILED DESCRIPTION OF THE PREFERRED EMBODIMENTS

Figure 1:
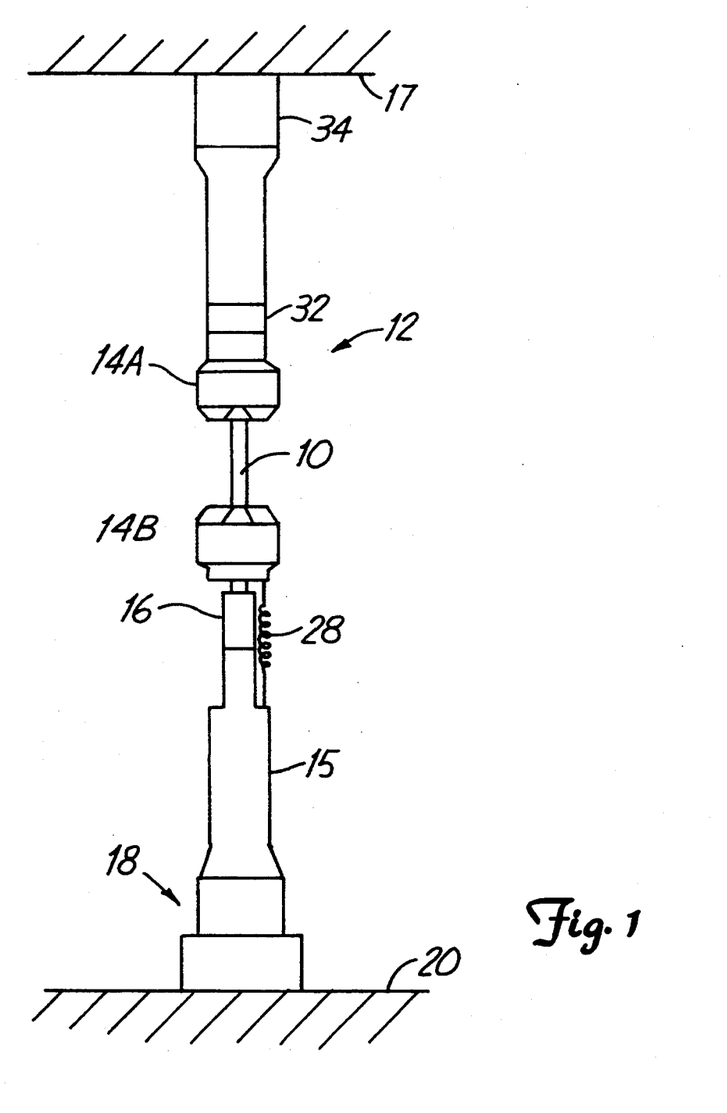
FIG. 1 is a schematic representation of a material testing system of the present invention.

A material testing system for applying force loads to a test specimen 10 is illustrated schematically in FIG. 1 at 12. The system 12 includes an upper holding member 14A and a lower holding member 14B that hold the test specimen 10 along a longitudinal axis. The lower holding member 14B is connected to an actuator 16 through which force loads are provided to the test specimen 10 and reacted against a reaction structure represented generally at 17 and a second actuator 18. The second actuator 18 also applies force loads to the test specimen 10, the second actuator 18 being secured to a stationary frame represented generally at surface 20.

Figure 2:
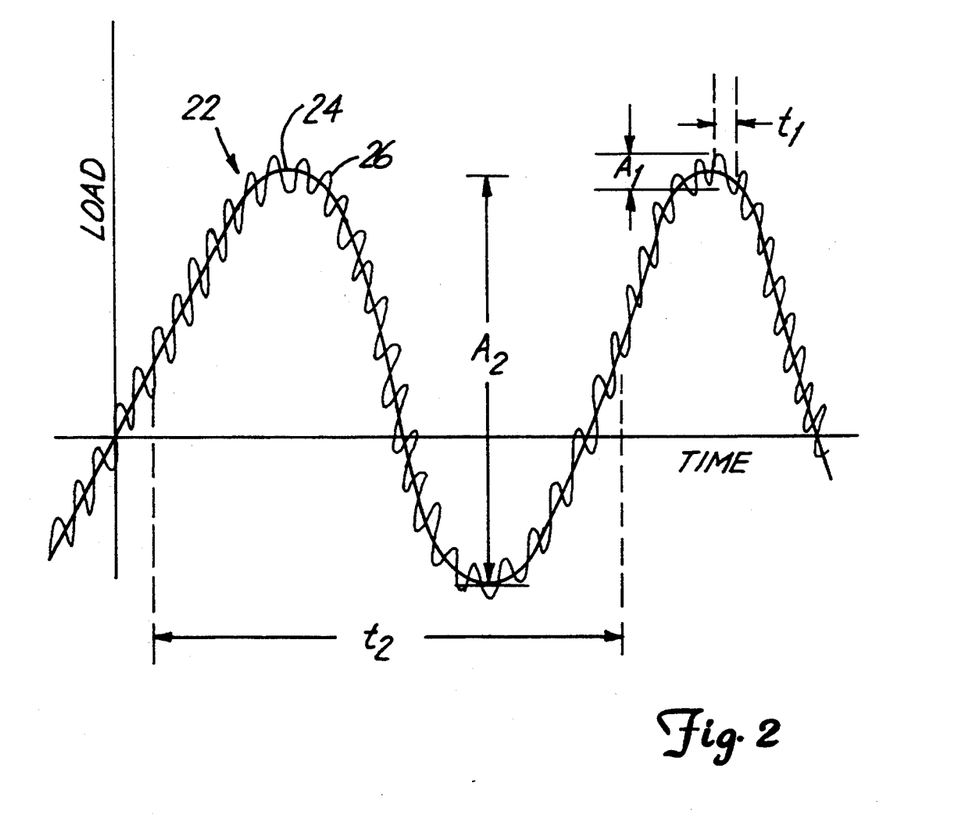
FIG. 2 is a graphical illustration of force loads applied to a test specimen.

Referring to FIG. 2, the actuators 16 and 18 provide combined or superimposed force loads 22 to the test specimen 10. As illustrated, the superimposed force loads 22 are cyclical and include a first force load component 26 having a first frequency $F_1$ corresponding to time period $T_1$ with a peak to peak amplitude $A_1$, and a second force load component 24 having a lower frequency $F_2$ corresponding to a longer time period $T_3$. The second force load component 24 has a peak to peak amplitude defined by $A_2$ which is typically more than the amplitude $A_1$ of the first force load component 26. Although illustrated with continuous sinusoidal wave forms, it is to be understood that the superimposed force load components 24 and 26 can take other forms as well as be non-continuous, being applied as desired during a testing cycle. Preferably, the actuator 18 provides the low frequency, high amplitude force load component 24, while the actuator 16 provides the high frequency, low amplitude force load component 26.

Referring back to FIG. 1, the actuator 18 includes a mass 15 that when displaced by an oil column (spring element), not shown, within the actuator, defines a natural frequency of the actuator 18. The frequency $F_1$ of the force load component 26 is chosen to be substantially higher than the natural frequency of the actuator 18, preferably at least twice as high. Generally, the frequency $F_2$ of the force load component 24 is less than the natural frequency of the actuator 18; however, this is not necessary.

A spring element 28 connected in parallel with the actuator 16 between the lower holding member 14B and the actuator 18 allows both of the force load components 24 and 26 to be applied to the test specimen 10 at the same time. The spring element 28 is substantially rigid for low frequencies such as $F_2$ and high amplitudes such as $A_2$ in order to transfer the force load 24 provided from the actuator 18 to the test specimen 10, while the spring element 28 is substantially compliant for high frequencies such as $F_2$ and low amplitudes such as $A_1$ allowing the force load component 26 provided from the actuator 16 to be transferred to the test specimen 10.

The supper holding member 14A is connected to the reaction structure 17 through series connected load cells 32 and 34. The load cells 32 and 34 provide representative signals proportional to each of the force load components 26 and 24, respectively. Although it is to be understood that one load cell could be used to measure both force load components, if desired.

Figure 3:
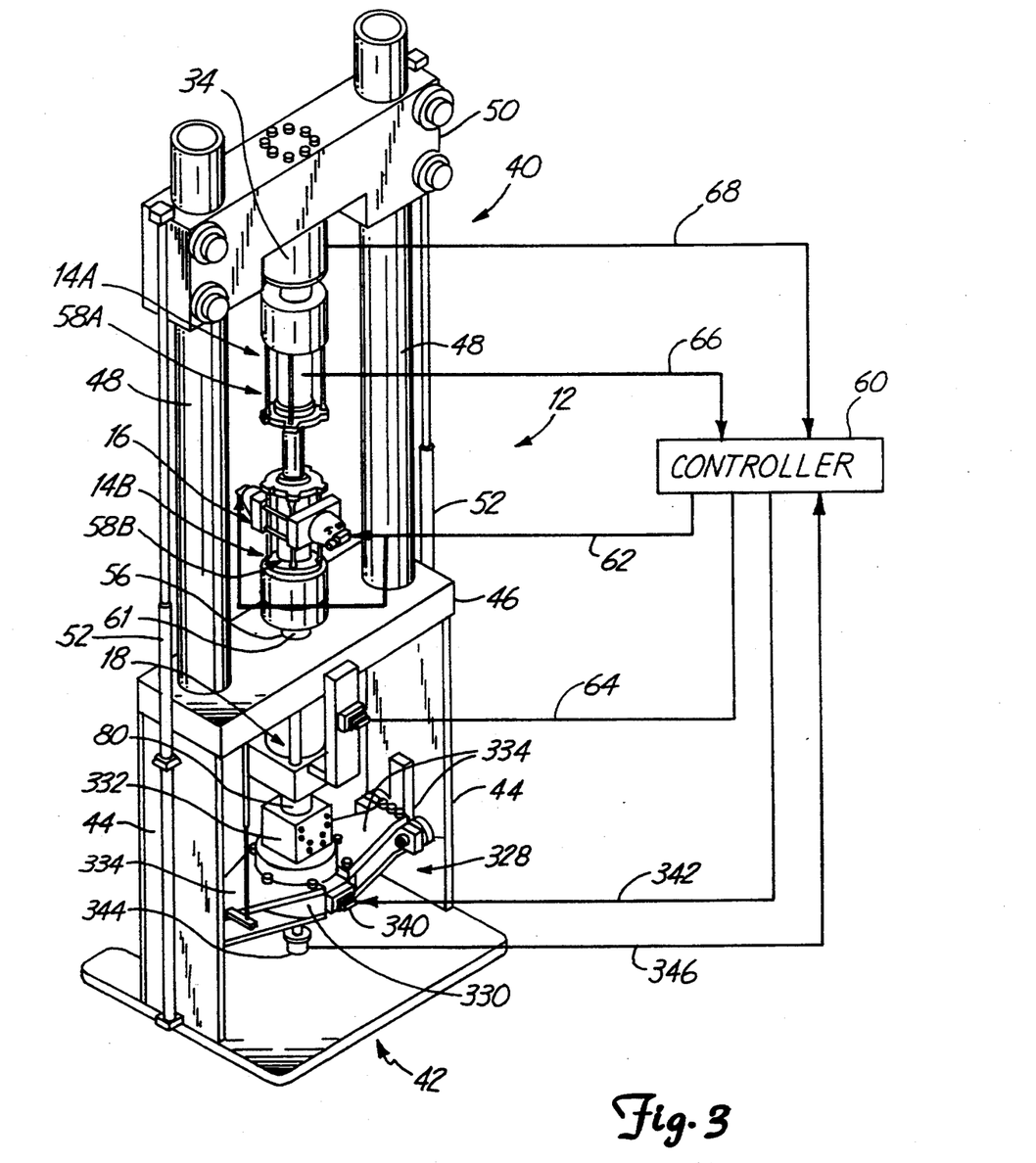
FIG. 3 is a perspective view of an embodiment of the present invention.

An embodiment of the material testing system 12 is illustrated in FIG. 3. The material system 12 includes a frame 40 having a base 42. A pair of support members 44 extend upwardly from the base 42 and are joined together by a crossbeam 46 which provides the stable support surface 20 of FIG. 1. A pair of support columns 48 extend upwardly from the crossbeam 46 to support a movable crosshead 50. The upper holding member 14A, load cell 32 (not shown) and load cell 34 are secured to the crosshead 50. The crosshead 50 and support columns 48 provide the reaction structure 17 illustrated in FIG. 1. Hydraulic lifts 52 move the crosshead 50 to selectively fixed positions.

The actuator 18 is joined to the crossbeam 46. A piston rod 61 of the actuator 18 projects through a suitable aperture 56 in the crossbeam 46. The lower grip member 14B is connected to the piston rod 61 and supports the test specimen 10 between the support columns 48. The actuator 16 attaches to the lower grip member 14B. In the embodiment illustrated, the spring element 28 comprises spring columns 58A in the upper holding member 14A, spring columns 58B and a spring tube 59 (FIG. 4) in the lower holding member 14B, the spring columns 58B and spring tube 59 being in parallel.

A control system 60 provides control signals along signal lines 62 and 64 to actuators 16 and 18, respectively, while signals received along lines 66 and 68 are proportional to the forces measured by the load cells 32 and 34, respectively.

Figure 4:
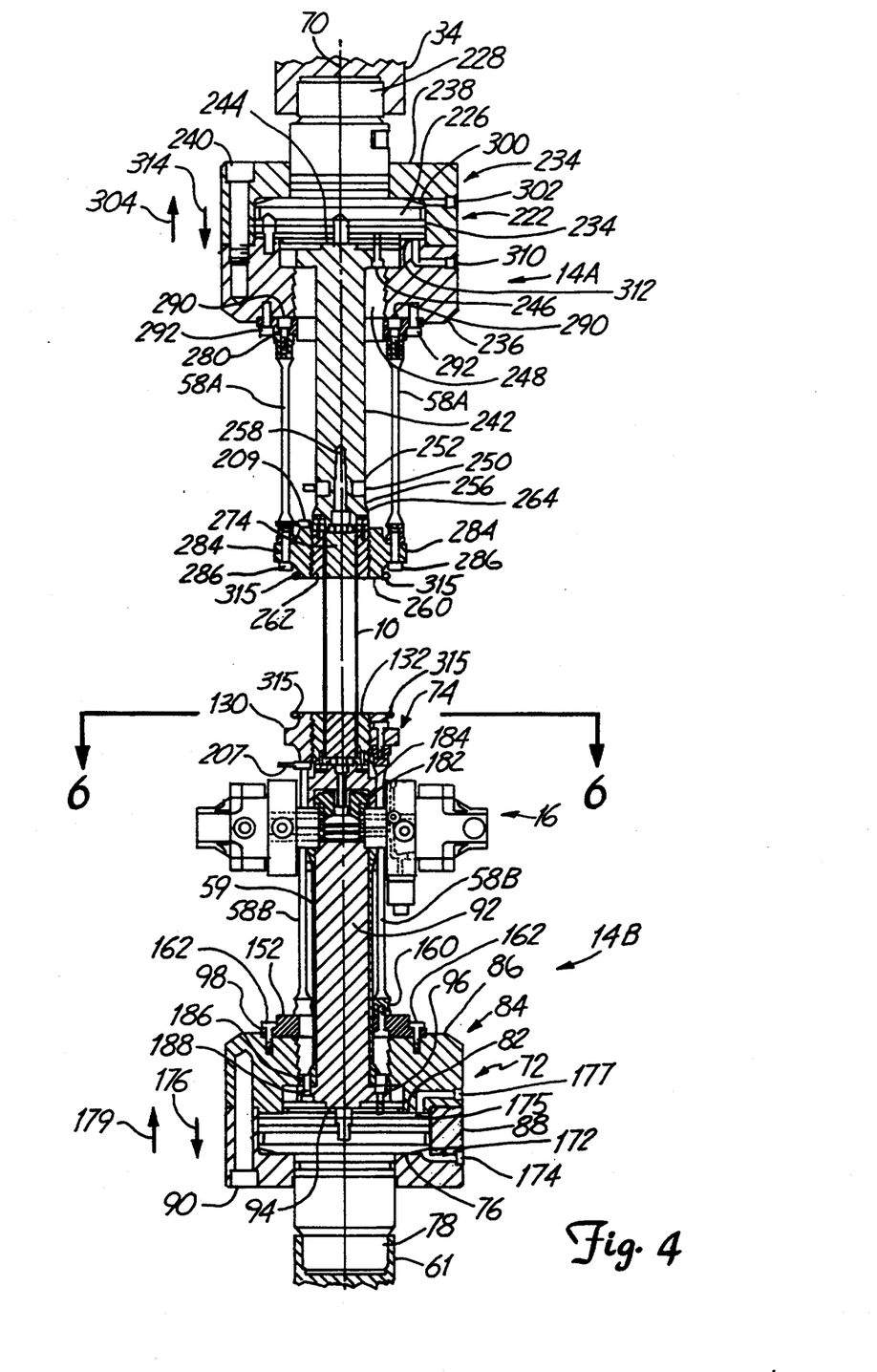
FIG. 4 is an enlarged sectional view of a portion of the embodiment of FIG. 3.

The upper holding member 14A, the lower holding member 14B and the actuator 16 along with the test specimen 10 are shown in detail in FIG. 4 aligned with a common longitudinal axis 70. In the embodiment illustrated, the holding members 14A and 14B are p reload clamps that when actuated provide a preload force upon the test specimen 10. When desired, the preload force is removed, which in turn allows easy removal of the test specimen 10 from the holding members 14A and 14B.

The holding member 14B includes an actuator portion 72 and a gripping portion 74. The actuator portion 72 includes a piston 76 having and end 78 that attaches to connecting rod 61 of the actuator 18. The piston 76 is located in a chamber 82 of an outer housing 84. The outer housing 84 is formed from housing sections 86 and 88 secured together with suitable fasteners one of which is illustrated at 90. A support column 92 having a centering mandril 94 is fastened to the piston 76 with a plurality of bolts, one of which is illustrated at 96. The support column 92 extends through an aperture 98 in the housing section 86 to the gripping portion 74.

Figure 5:
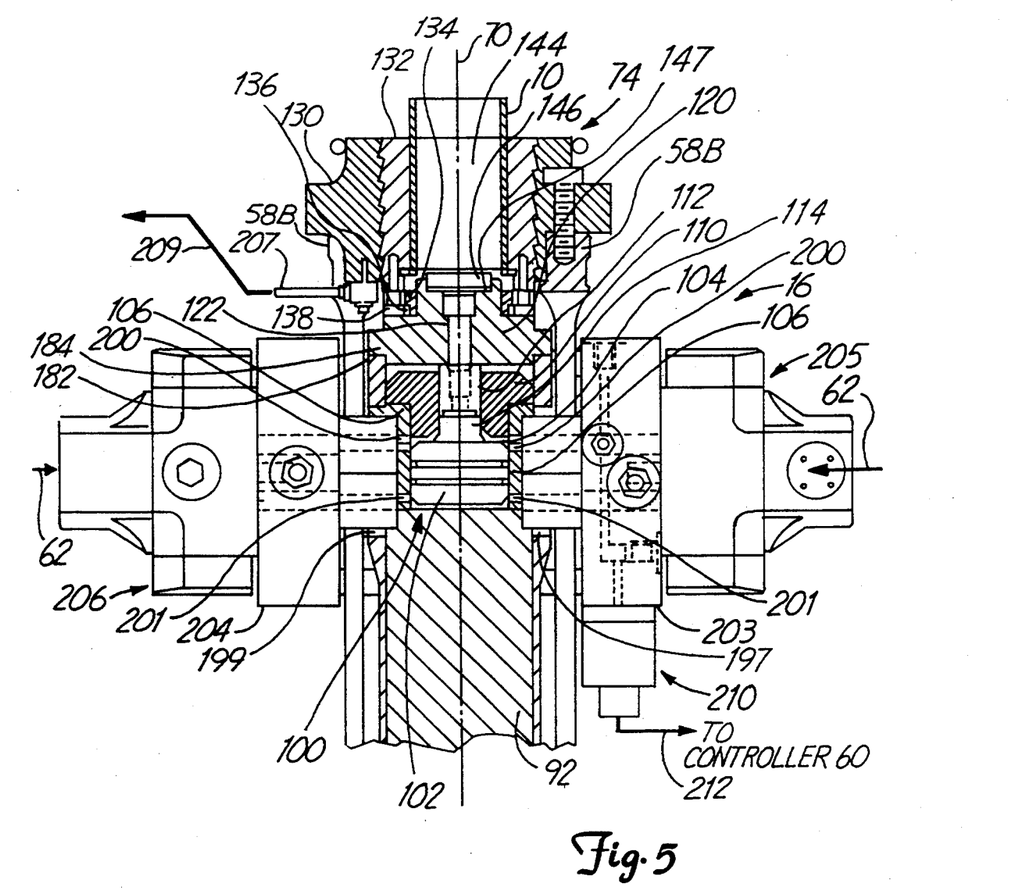
FIG. 5 is an enlarged sectional view of a portion of FIG. 4.

Referring also to FIG. 5, the actuator 16 is mounted to an end 100 of the support column 92. The actuator 16 includes a selectively displaceable piston 102. The piston 102 is located in a chamber 104 formed in the end 100 of the support column 92 with a cylinder wall 106. Preferably, the wall 106 is cylindrical and integral with the support column 92. An endcap 110 is joined to the wall 106 above the chamber 104 with suitable threaded fasteners, not shown. The endcap 110 includes an aperture 112 allowing a connecting rod 114 attached to the piston 102 to extend therethrough. At an end opposite piston 102, the connecting rod 114 is secured to a support plate 120 with a suitable fastener 122.

Figure 6:
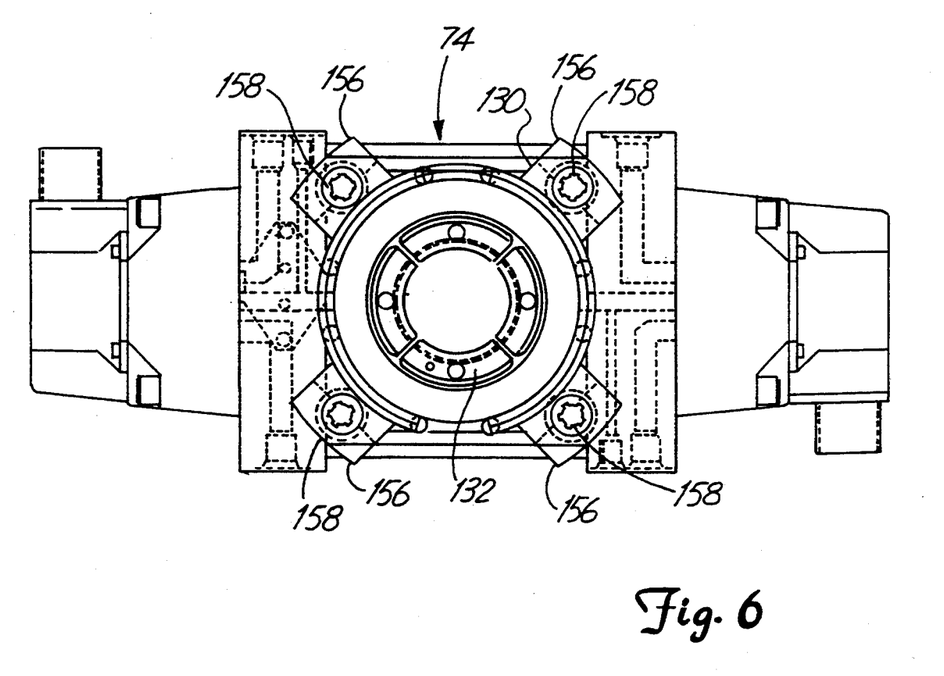
FIG. 6 is a sectional view taken along line 6—6 of FIG. 4.

The gripping portion 74 is positioned on the support plate 120. Referring also to FIG. 6, the gripping portion 74 includes an outer grip housing 130 and an inner collet 132. The inner collet 132 is fastened to a centering ring 134 having T-slot apertures 136 for the heads of a plurality of fasteners 138. The T-slot apertures 136 allow the collet 132 and fasteners 138 to move radially relative to the longitudinal axis 70 when the collet 132 compresses inwardly to grip the test specimen 10. As illustrated herein, the test specimen 10 is cylindrical and in order to prevent inward collapse of the test specimen 10 during application of the preload force, a support plug 144 is located within the test specimen 10. The support plug 144 includes a centering mandril 146 which engages a recess 147 in the support plate 120. The spring columns 58B connected between the outer grip housing 130 and a support ring 152 (FIG. 4) transfer the preload force from the actuator portion 72 to the gripping portion 74. As illustrated in FIG. 6, preferably four spring columns are used being positioned at equal angular intervals about the longitudinal axis 70. The spring columns 58B are fastened to the outer grip housing 130 on extending support tabs 156 with suitable threaded fasteners 158. At ends opposite outer grip housing 130, the spring columns 58B are fastened to the support ring 152 with fasteners 160, one of which is illustrated in FIG. 4. The support ring 152 is securely fastened to the housing section 86 with a plurality of fasteners 162.

The preload force is applied to the test specimen 10 by the gripping portion 74 when a chamber 172 formed between the piston 82 and the outer housing section 88 is pressurized through a port 174. Pressurization of the chamber 174 causes the housing 84 to be displaced relative to the piston 82 in a direction indicated by arrow 176. Movement of the housing 84 in turn displaces the support ring 152, the spring columns 58B and the outer grip housing 130 also in the direction indicated by arrow 176. Due to the angled surfaces between the outer grip housing 130 and the inner collet 132, a force perpendicular to the longitudinal axis 70 is developed to grip the test specimen 10 along with a downward force component upon the support plate 120. The downward force component is reacted back to the piston 82 through the spring tube 59 having a first end 182 contacting an extending flange 184 of the support plate 120, and a second end 186 which is fastened to the support column 92 with a plurality of suitable fasteners, one of which is shown at 188. The spring columns 58B and spring tube 59 are substantially rigid for force loads applied through the use of the actuator 18 thus transferring these force loads to the test specimen 10, and are substantially compliant to force loads transmitted to the test specimen through the actuator 16. A release port 177 is connected to a chamber 175 which when pressurized causes upward movement of the housing 84 and structure thereattached in a direction indicated by arrow 179 to release the preload force.

Referring back to FIG. 5, pressure ports 200 and 201 formed through the cylinder walls 106 selectively pressurize opposite sides of the piston 102 to provide the high frequency force component 26. Manifolds 203 and 204 extend through apertures 197 and 199 formed in the spring tube 59 and connect the pressure ports 200 and 201 to suitable servovalves 205 and 206, respectively, which are controlled by the controller 60 using the control lines 62. An unequal area differential pressure transducer 210 measures and provides a signal to the controller 60 along signal line 212 proportional to the force applied by the actuator 16. This force is computed using the pressures applied to opposite sides of the piston 102. An accelerometer 207 (FIG. 5) is secured to the outer grip housing 130 and provides a signal along a signal line 209 to the controller 60 that is proportional to the acceleration experienced by the gripping portion 74. With a second accelerometer 209 also joined to the upper holding member 14A (FIG. 4) and connected to suitable circuitry, not shown, that integrates the acceration signals to provide a signal proportional to displacement of the test specimen 10, as is well known in the art.

Referring back to FIG. 4, the upper holding member 14A also includes an actuator portion 222 and a gripping portion 224. The actuator portion 222 includes a piston 226 having an end 228 that attaches to the load cell 34. The piston 226 is located in a chamber 232 of an outer housing 234. The outer housing 234 is formed from housing sections 236 and 238 secured together with suitable fasteners one of which is illustrated at 240. A support column 242 having a centering mandril 244 is fastened to the piston 226 with a plurality of bolts, one of which is illustrated at 246. The support column 242 extends through an aperture 248 in the housing section 236 to the gripping portion 224.

In the embodiment illustrated, the load cell 32 (FIG. 1) comprises a piezoelectric washer 250 mounted to an end 252 of the support column 242. A endcap 256 with a suitable fastener 258 extending therethrough and threaded into the support column 242 secures the piezoelectric washer 250 in place.

The gripping portion 224 is positioned on the endcap 256. Like the gripping portion 74, the gripping portion 224 includes an outer grip housing 260 and an inner collet 262. The inner collet 262 is fastened to a centering ring 264 having T-slot apertures 266 for the heads of a plurality of fasteners 268. The T-slot apertures 268 allow the collet 262 and fasteners 268 to move radially relative to the longitudinal axis 70 when the collet 262 compresses inwardly to grip the test specimen 10 and provide the preload force. In order to prevent inward collapse of the test specimen 10 during application of the preload force, a support plug 274 is located within the test specimen 10. The spring columns 58A connected between the outer grip housing 260 and a support ring 280 transfer the preload force from the actuator portion 72 to the gripping portion 74. Like the lower holding member 14A, preferably four spring columns 58A are used being positioned at equal angular intervals about the longitudinal axis 70. The spring columns 58A are fastened to the outer grip housing 260 on extending support tabs 284 with suitable threaded fasteners 286. At ends opposite outer grip housing 260, the spring columns 58A are fastened to the support ring 280 with fasteners 290. The support ring 280 is securely fastened to the housing section 236 with a plurality of fasteners 292.

The preload force is applied to the test specimen 10 by the gripping portion 224 when a chamber 300 formed between the piston 226 and the outer housing section 238 is pressurized through a portion 302. Pressurization of the chamber 300 causes the housing 234 to be displaced relative to the piston 226 in a direction indicated by arrow 304. Movement of the housing 234 in turn displaces the support ring 280, the spring columns 58A and the outer grip housing 260 also in the direction indicated by arrow 304. Due to the angled surfaces between the outer grip housing 260 and the inner collet 262, a force perpendicular to the longitudinal axis 70 is developed to grip the test specimen 10 along with an upward force component upon the endcap 256. The upward force component is reacted back to the piston 226 through the support column 242. A release port 310 is connected to a chamber 312 which when pressurized causes downward movement of the housing 234 and structure thereattached in a direction indicated by arrow 314 to release the preload force.

Commonly, the test specimen 10 is maintained at a desired temperature. If the test specimen 10 is heated, cooling tubes 315 attached to the outer housing 130 and 260 and connected to a suitable cooling source, not shown, can be used to prevent overheating of the gripping portions 74 and 224.

In a further preferred embodiment, the material testing system 12 also applies torsional loads to the test specimen 10. Referring back to FIG. 3, a torsional loading system 328 includes a rotary actuator 330 connected to the connecting rod 61 of the actuator 18 with a suitable coupler 332. Plates 334 joined to the support members 44 react torsion loads back to the frame 40. A suitable servovalve 340 receives control signals from the controller 60 along a signal line 342, while a transducer 344 provides a signal along a signal line 346 back to the controller 60 proportional to the angular displacement of the connecting rod 61. When the torsional loading system 328 is used, elements in the load train such as spring columns 58A and 58B, and spring tube 59 must have sufficient torsional stiffness to transfer the torsional loads to the test specimen 10, the load cell 34 further providing a signal proportional to torque applied.

Figure 7:
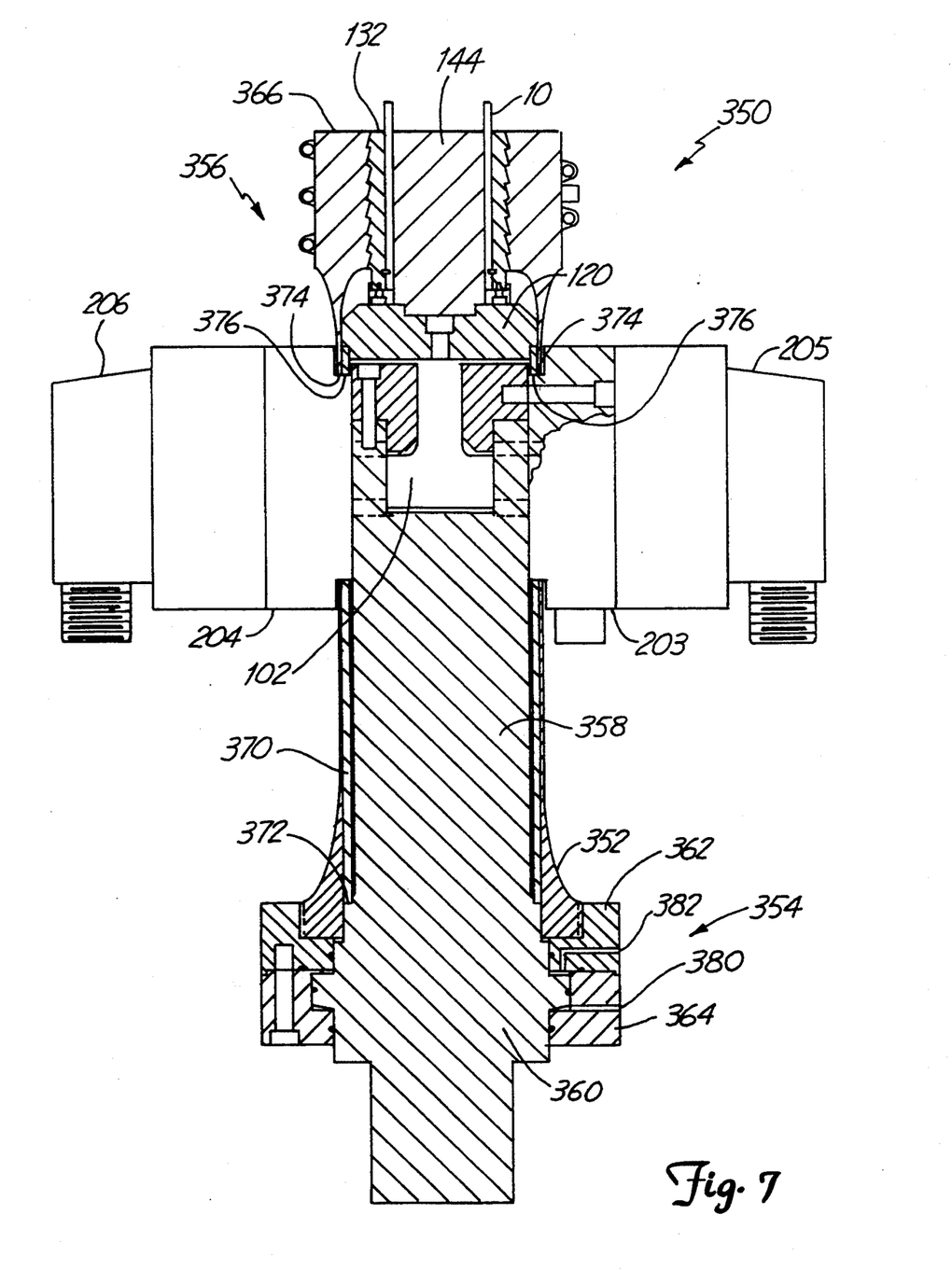
FIG. 7 is a second embodiment of a holding member.

FIG. 7 illustrates a second embodiment of a holding member 350 wherein the spring columns have been replaced with an outer tube 352. The holding member 350 has an actuator portion 354 and a gripping portion 356. The actuator portion 354 includes an integral support column 358 and piston 360, the piston 360 is surrounded by a housing formed from housing sections 362 and 364. The outer tube 352 threadably mates with the housing section 362 and forms an outer grip housing 366 at an end opposite the housing section 362. An inner tube 370 contacts an annular flange 372 of the piston 360 and the support plate 120. Both the outer tube 352 and the inner tube 370 include apertures 374 and 376, respectively, that allow the manifolds 203 and 204 to be secured to the support column 358. Operation of the gripping portion 356 is otherwise similar to the holding member 14B described above with selective pressurization through a clamping port 380 and a release port 382.

In summary, the present invention provides a material testing system capable of applying multiple force load components to a test specimen simultaneously. By using a spring element connected in parallel with an actuator, the two of which being connected in series with the test specimen and a second actuator, the system is compact and capable of applying desired force loads.

Although the present invention has ben described with reference to preferred embodiments, workers skilled in the art will recognize that changes may be made in form and detail without departing from the spirit and scope of the invention. For instance, although described with hydraulically operating actuators, it is to be understood that other actuators such as piezoelectric, electromagnetic and magnetostrictive actuators are also equally well suited for applying force loads to the test specimen.

What is claimed is:

1. A material testing apparatus for applying force loads to a test specimen, the material testing apparatus comprising:
   a frame;
   holding means for holding the test specimen on the frame; and
   force means for applying simultaneous force loads, the force means comprising:
      first actuator means connected to the holding means for applying a first force load;
      second actuator means connected to the first actuator means for applying a second force load; and
      spring means connected to the holding means and the second actuator means in parallel with the first actuator means for transferring the second force load to the holding means.

2. The material testing apparatus of claim 1 wherein the first force load has a first frequency and the second force load has a second frequency different than the first frequency.

3. The material testing apparatus of claim 2 wherein the first frequency is greater than the second frequency.

4. The material testing apparatus of claim 3 wherein the first force load and the second force load are sinusoidal and an amplitude of the second force load is greater than an amplitude of the first force load.

5. The material testing apparatus of claim 1 wherein the force means includes means for applying a torsional load to the test specimen.

6. A material testing apparatus for applying force loads to a test specimen, the material testing apparatus comprising:
   a frame;
   holding means for holding the test specimen on the frame, the holding means comprising a first grip assembly and a second grip assembly gripping the test specimen at opposite ends;
   force means for applying simultaneous force loads, the force means comprising:
      first actuator means connected to the first grip assembly for applying a first force load;
      second actuator means connected to the first actuator means for applying a second force load; and
      spring means connected to the first grip assembly and the second actuator means in parallel with the first actuator means for transferring the second force load to the first grip assembly.

7. The material testing apparatus of claim 6 wherein the first grip assembly includes gripping means for gripping the test specimen and operating means for operating the gripping means.

8. The material testing apparatus of claim 7 wherein the first actuator is joined between the gripping means and the operating means.

9. The material testing apparatus of claim 8 wherein the spring means is joined between the gripping means and the operating means.

10. The material testing apparatus of claim 9 and further comprising connecting means for connecting the operating means to the gripping means.

11. The material testing apparatus of claim 10 wherein the connecting means comprises a support column.

12. The material testing apparatus of claim 11 wherein the first actuator is connected to the support column and the gripping means.

13. The material testing apparatus of claim 12 wherein the operating means comprises a piston selectively displaceable in a chamber of a housing, the support column being attached to the piston.

14. The material testing apparatus of claim 13 wherein the spring means comprises a spring tube operably connected to the gripping means and the piston, the spring tube being positioned concentrically about the support column.

15. The material testing apparatus of claim 14 wherein the spring means further comprises a plurality of spring columns positioned about the support column and connecting the housing to the gripping means.

16. The material testing apparatus of claim 14 wherein the spring means further comprises a second spring tube positioned about the support column and connecting the housing to the gripping means.

17. The material testing apparatus of claim 9 wherein the spring means comprises two spring elements in parallel.

18. A measuring apparatus for measuring force loads applied to a test specimen from a material testing system, the measuring apparatus comprising:
   gripping means for selectively gripping and releasing the test specimen;
   operating means for operating the gripping means;
   measuring means for measuring force loads applied to the test specimen, the measuring means joining the operating means to the gripping means.

19. The measuring apparatus of claim 18 wherein the measuring means includes a load cell and spring means connected in parallel between the gripping means and the operating means, the spring means transferring movement of the operating means to the gripping means, the spring means being substantially compliant for force loads having a selected frequency wherein the load cell measures the force load applied to the test specimen at the selected frequency.

20. The measuring apparatus of claim 19 wherein the operating means comprises an actuator.

21. The measuring apparatus of claim 20 wherein the spring means is substantially rigid for force loads having a second frequency, the measuring apparatus further comprising a second load cell connected to the actuator on a side opposite the first-mentioned load cell, the second load cell measuring the force loads applied to the test specimen at the second frequency.

22. The measuring apparatus of claim 21 wherein the actuator includes a housing and a piston being connected to the first-mentioned load cell, the housing being moveable relative to the piston, and the spring means being connected to the housing.

23. The measuring apparatus of claim 22 wherein the actuator comprises a hydraulic actuator.

24. The measuring apparatus of claim 18 wherein the operating means comprises:
- a housing having a chamber; and
- a piston disposed in the chamber, the housing moveable relative to the piston; and wherein the measuring means comprises:
- a load cell joined to the piston and to the gripping means; and
- spring means joined the housing and to the gripping means for transferring movement of the housing to the gripping means.

* * * * *